United States Patent

Smith

[11] Patent Number: 6,099,543
[45] Date of Patent: Aug. 8, 2000

[54] OPHTHALMIC SURGICAL BLADE

[76] Inventor: Thomas C. Smith, 13125 Wilcox Rd., #6B4, Largo, Fla. 33774

[21] Appl. No.: 09/299,506
[22] Filed: Apr. 26, 1999

Related U.S. Application Data

[63] Continuation-in-part of application No. 09/040,800, Mar. 18, 1998.
[51] Int. Cl.⁷ .................................................. A61B 17/32
[52] U.S. Cl. ................................................................ 606/167
[58] Field of Search .................................. 606/167, 159, 606/166, 183, 185; 76/104; 30/346.55

[56] References Cited

U.S. PATENT DOCUMENTS

| | | | |
|---|---|---|---|
| 5,352,233 | 10/1994 | Anis | 606/167 |
| 5,423,840 | 6/1995 | Casebeer et al. | 606/167 |
| 5,713,915 | 2/1998 | Van Heugten et al. | 606/167 |
| 5,799,549 | 9/1998 | Decker et al. | |

*Primary Examiner*—Michael Buiz
*Assistant Examiner*—(Jackie)Tan-Uyen T. Ho
*Attorney, Agent, or Firm*—Dennis G. LaPointe; Mason & Associates, PA

[57] ABSTRACT

A blade has a proximal end and a distal end and a central axis of elongation. The proximal end is generally rectangular cubic with a flat profile having top and bottom surfaces and short sidewalls, with each sidewall made up of two edges meeting to define an angle of approximately 95° to 160°. The apex of this angle is unsharpened and these sidewalls comprise guide means for guiding movements of the blade through an opening created by the cutting surfaces located on the distal end thereof The distal end of the blade includes a cutting surface made up of a sharp pointed tip with the cutting edges proximal of the tip defining an angle of 40° to 140° in one embodiment or 10° to 60° in another embodiment wherein these cutting edges further extend laterally and proximally to define an angle therebetween of 40° to 140° about a central axis of elongation. Two angled surfaces extend laterally and proximally to either side of the tip, each making an angle of 15° to 50° with the bottom surface of the blade. The tip is located between the planes defined by the top and bottom surfaces of the blade. The inventive blade is made from diamond. However, materials such as stainless steel, sapphire, ruby, cubic zirconia, pure or composite ceramics, ceramic metal composites, and titanium alloys can be substituted for the diamond.

34 Claims, 5 Drawing Sheets

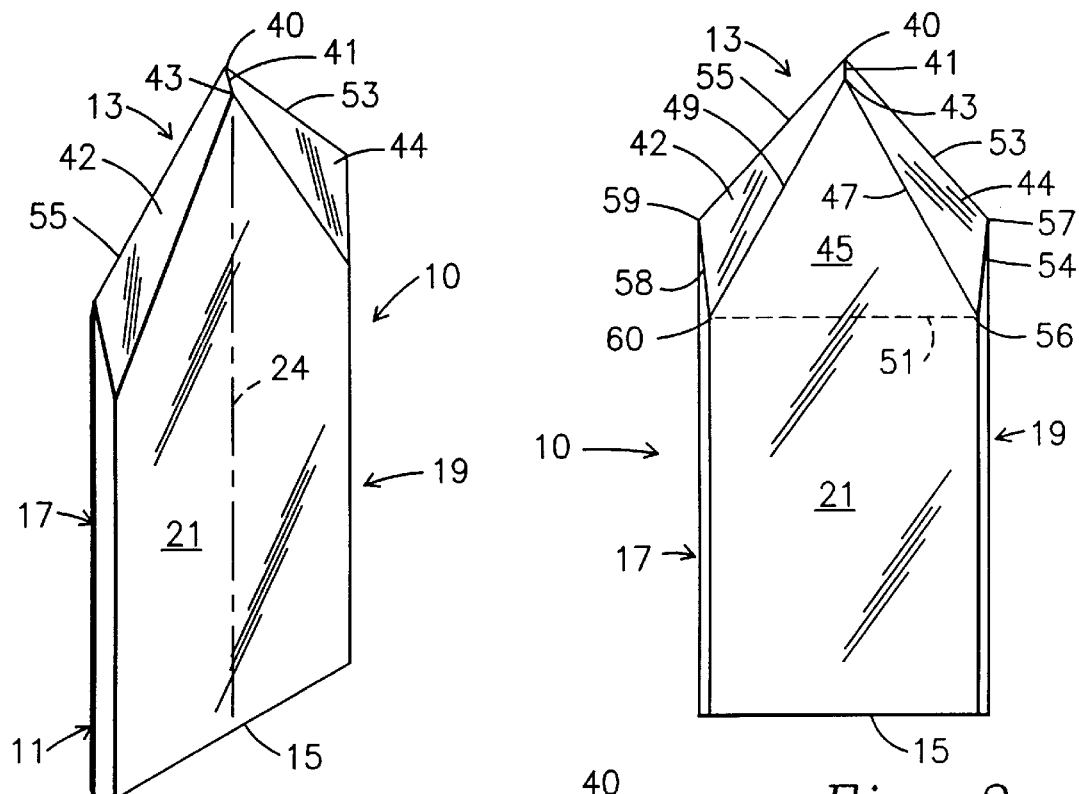
Fig. 1
Fig. 2
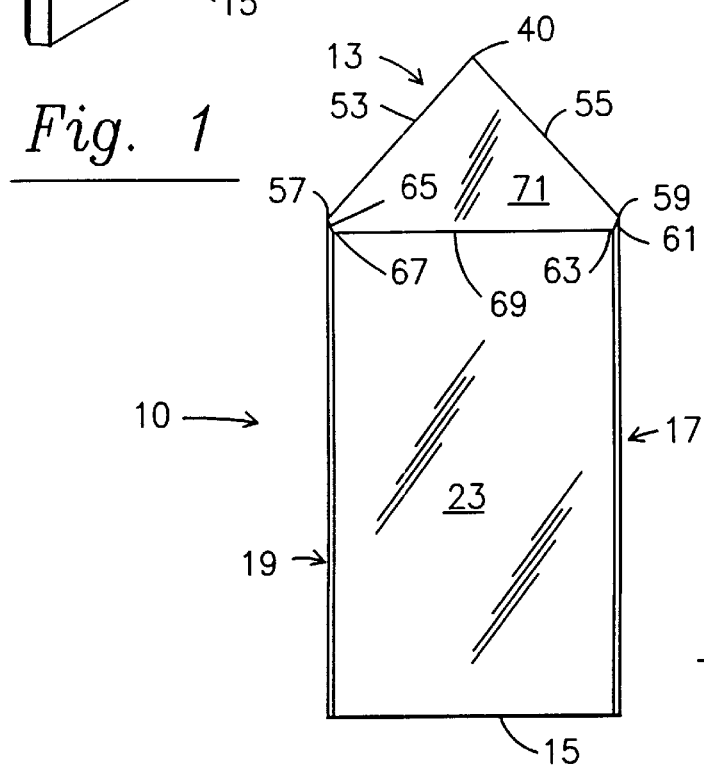
Fig. 3

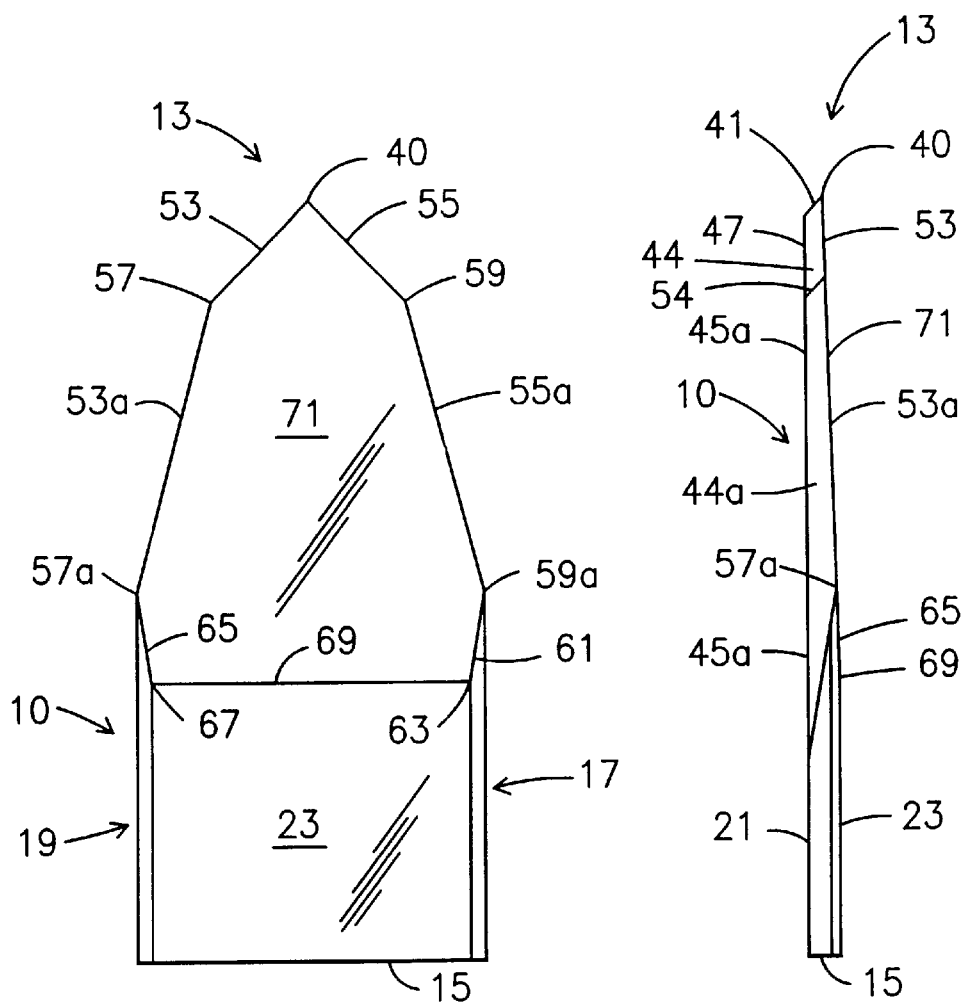
Fig. 8
Fig. 9
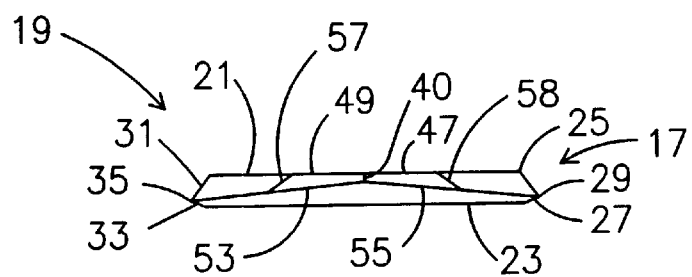
Fig. 10

OPHTHALMIC SURGICAL BLADE

RELATED APPLICATION

This application is a continuation-in-part of U.S. patent application Ser. No. 09/040,800 filed Mar. 18, 1998.

BACKGROUND OF THE INVENTION

1. Field of the invention

The present invention relates to an ophthalmic surgical blade having hard single bevel edges.

2. Description of related art

Performance of eye surgery using an ophthalmic surgical blade has become commonplace. Numerous diverse blade designs are employed in such surgeries and each blade has its advantages and disadvantages.

During the performance of eye surgery, several problems arise caused by various features of prior art blades. For example, it is important to create a geodesic incision through the cornea at the proper angle and with the required pressure to facilitate self sealing characteristics of the wound. It is desirable, when making such an incision, to avoid deformation of eye tissues and to prevent inadvertent tearing or widening of the extremities of the incision such as are caused by sharp or squared sides on the width of the blade. Additionally, a blade should be able to create a self-sealing wound such as would be created when individual corneal layers are gradiently cut rather than slashed by the blade. A contoured cut properly aligns itself while a straight slash cut does not do so.

Known related art includes U.S. Pat. No. 5,217,476 to Wishinsky which discloses a surgical knife blade and method of performing cataract surgery utilizing a surgical knife blade. While embodiments of the Wishinsky knife blade, particularly those shown in FIGS. 1–5, are symmetrical, the present invention distinguishes from the teachings of Wishinsky as contemplating a blade wherein the lateral surfaces thereof are unsharpened and merely act as guide means.

U.S. Pat. No. 5,222,967 to Casebeer et al. discloses a keratorefractive diamond blade and surgical method wherein the blade is asymmetrical about a central longitudinal axis. The same may be said for U.S. Pat. No. 5,423,840, also to Casebeer et al. The present invention differs from the teachings of these patents as contemplating an ophthalmic blade that is symmetrical about a central longitudinal axis and has side surfaces that are not sharpened but, rather, merely function as guide means.

U.S. Pat. No. 5,352,233 to Anis discloses a scalpel and technique for using a scalpel including one embodiment showing a blade that is symmetrical about a longitudinal axis of elongation thereof. This embodiment shows sharp corners at the widest portions of the blade and a blade edge that is equidistant from the top and bottom surfaces of the blade. The present invention differs from the teachings of Anis as having side edges that are not sharpened and that merely perform a guiding function as well as a sharpened edge that is not equidistant from the top and bottom surfaces of the blade.

Other known related art includes U.S. Pat. No. 5,370,652 to Kellan which discloses a surgical knife blade for making sutureless incisions in the eye and methods therefor. The blades of Kellan are symmetrical with respect to a longitudinal axis of elongation thereof. In one embodiment, the blade edge includes a sharpened central point and side edges that are sharp as well. Other embodiments include curved cutting surfaces wherein a central point is not included. In each embodiment, the cutting edge is in a plane common with the bottom surface of the blade. The present invention differs from the teachings of Kellan as contemplating a blade symmetrical with respect to a longitudinal axis of elongation thereof having a central point, side edges that are not sharpened and merely provide guiding surfaces, and wherein the cutting edge is not equidistantly located between the top and bottom surfaces of the blade and is not in any plane common with either of those surfaces.

U.S. Pat. No. 5,376,099 to Ellis et al. discloses an undercut diamond surgical blade and method of using same. Embodiments of Ellis et al. include cutting surfaces on a blade sidewall and a cutting edge equidistantly spaced between the top and bottom surfaces thereof. In contrast, the present invention contemplates a blade having a pointed end aligned with an axis of elongation thereof with side edges unsharpened and comprising guide means and with the cutting, edge being non-equidistantly spaced between the top and bottom surfaces thereof.

SUMMARY OF THE INVENTION

The present invention relates to an ophthalmic surgical blade having hard single bevel edges. The present invention includes the following interrelated objects, aspects and features:

(1) In a first aspect, the inventive blade has a proximal end and a distal end and a central axis of elongation. The proximal end is generally rectangular cubic with a flat profile having top and bottom surfaces and short sidewalls, with each sidewall made up of two edges meeting to define, therebetween, an angle of approximately 95° to 160°. The apex of this angle is unsharpened and these sidewalls comprise guide means for guiding movements of the blade through an opening created by the cutting surfaces located on the distal end thereof.

(2) The distal end includes a cutting surface made up of a plurality of interrelated edges and facets. The distal end of the blade defines a sharp pointed tip with the cutting edges proximal of the tip defining an angle of 40° to 140°. An edge extends from the tip a short distance proximally aligned with the central axis of elongation, and two angled surfaces extend laterally and proximally to either side of this edge with these surfaces having distal edges that define the 40° to 140° angle described above. These distal edges extend proximally from the absolute distal tip of the blade to termination points coinciding with a bottom surface of the blade. The absolute distal tip is located between the planes defined by the top and bottom surfaces of the blade. The proximal termination of the edge described above as extending along the longitudinal axis of elongation of the blade comprises the distal point of termination of proximal edges of the two angled surfaces, which proximal edges extend distally to termination points on the top surface of the blade. The distal end optionally includes additional cutting surfaces wherein the distal end of the blade first defines a sharp pointed tip with the cutting edges proximal of the tip defining an angle therebetween of 10° to 60°. The cutting edges then extend laterally and proximally from a predetermined point of termination of the cutting edges emanating from the pointed tip and, the extended cutting edges defining an angle therebetween of 40° to 140° about the central axis of elongation.

(3) These proximal edges of the blade define therebetween a first generally triangular or polygonal surface and the distal edges of the blade define a second generally triangular or polygonal surface. In the preferred embodiment of the present invention, the first generally triangular or polygonal surface is coplanar with the top surface of the blade. The first generally triangular or polygonal surface makes an angle with the second generally triangular or polygonal surface of approximately 1° to 10°. Looking at the angled surfaces, each of which is, in part, defined by a proximal edge and a distal edge, these angled surfaces make an angle with the bottom surface of the blade of approximately 15° to 50° with the range of 20° to 27° being preferred.

(4) In the preferred embodiment of the present invention, the blade has a width of 0.8 to 7.0 millimeters and a thickness of from 90 to 625 microns.

(5) The inventive blade may be made from diamond, however, materials such as stainless steel, sapphire, ruby, cubic zirconia, pure or composite ceramics, ceramic metal composites, and titanium alloys can be substituted for the diamond.

(6) In the preferred embodiment, where the material from which the blade is made of metal, the blade is suitably coated on both sides with a material that is dissimilar to the blade material but harder than the blade material. The coating should have zero porosity, strong adhesion to the substrate surface, fracture resistance, insolubility in typical cleaning solutions, and non-reactivity with respect to body tissues and chemicals. The coating material should be sufficiently resilient, corrosion resistant and biocompatible. The coating on the surgical blade may be applied by chemical or physical vapor deposition; flame deposition; sputtering; ion plating; ion, neutral or electron beam deposition; surface conversion; pulsed laser deposition; vapor jet deposition; molecular beam epitaxy or lamination with heat and/or pressure after which the blade is sharpened on one side of each edge only. The cutting edge is then composed of the hard coating honed to a sub-micron edge radius of less than 0.1 micron.

Accordingly, it is a first object of the present invention to provide an ophthalmic surgical blade having hard single bevel edges.

It is a further object of the present invention to provide such a blade having a cutting tip with cutting edges emanating therefrom defining an angle in the range of 40° to 140°.

It is a further object of the present invention to provide such a blade wherein beveled surfaces emanating proximally from the tip have surfaces defining an angle of between 15° to 50° with respect to a bottom surface of the blade.

It is a still further object of the present invention to provide such a blade having an approximate thickness of 90 to 625 microns and an approximate width of 0.8 to 7.0 millimeters.

It is a yet further object of the present invention to provide such a blade having side edges, each of which is made up of two surfaces meeting at an angle of between 95° to 160° at an unsharpened apex.

These and other objects, aspects and features of the present invention will be better understood from the following detailed description of the preferred embodiments when read in conjunction with the appended drawing figures.

BRIEF DESCRIPTION OF THE DRAWINGS

FIG. 1 is a perspective view of the inventive blade.

FIG. 2 is a top view of the inventive blade shown in FIG. 1.

FIG. 3 is a bottom view of the inventive blade shown in FIG. 1.

FIG. 8 is a bottom view of the inventive blade shown in FIG. 6.

FIG. 9 is an enlarges side view of the inventive blade shown in FIG. 6, of which the other side is identical.

FIG. 10 is a front view of the inventive blade shown in FIG. 6.

DETAILED DESCRIPTION OF THE INVENTION

Figures 4, 5:
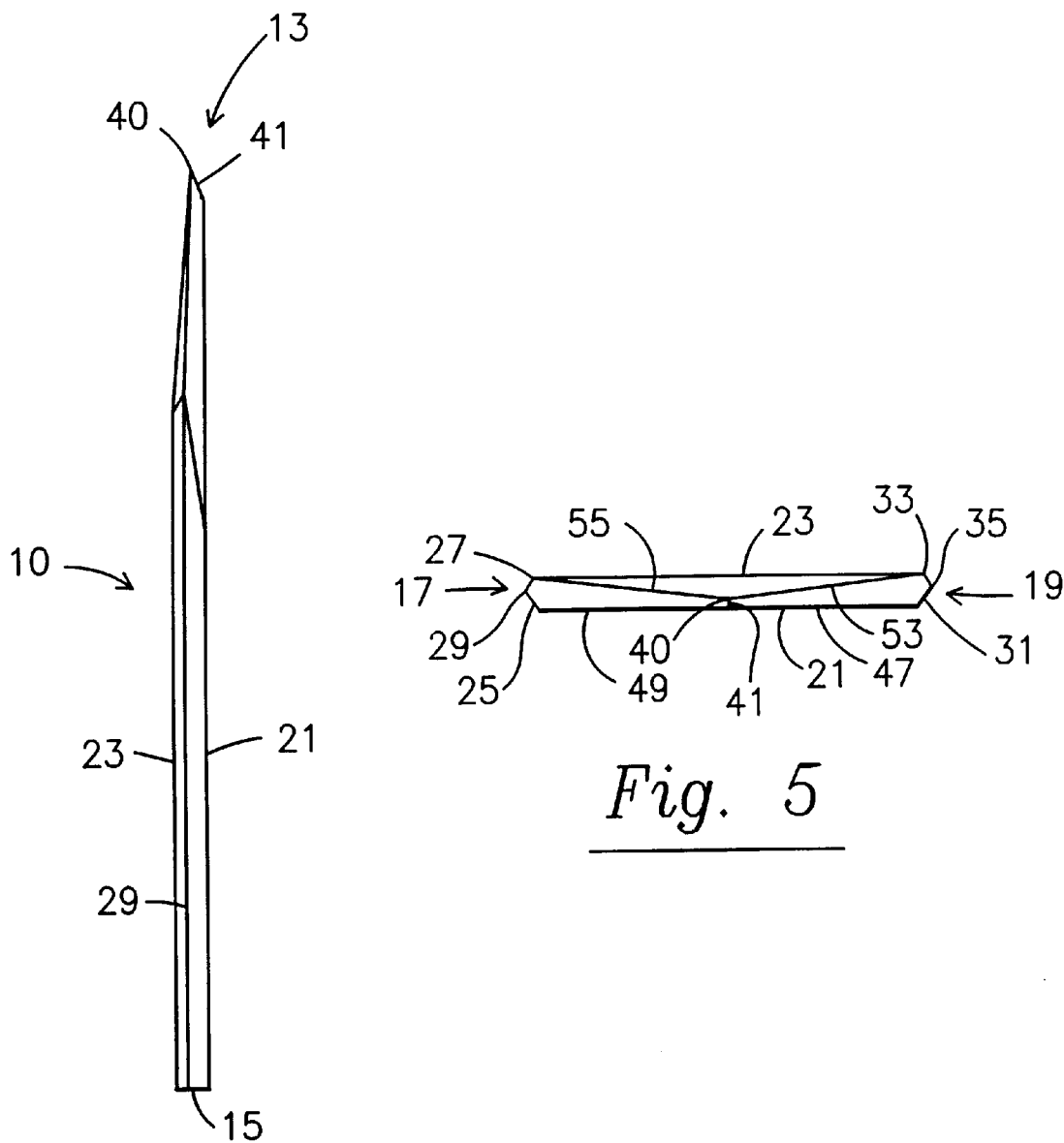
FIG. 4 is an enlarged side view of the inventive blade shown in FIG. 1, of which the other side is identical.
FIG. 5 is a front view of the inventive blade shown in FIG. 1.
Figure 6:
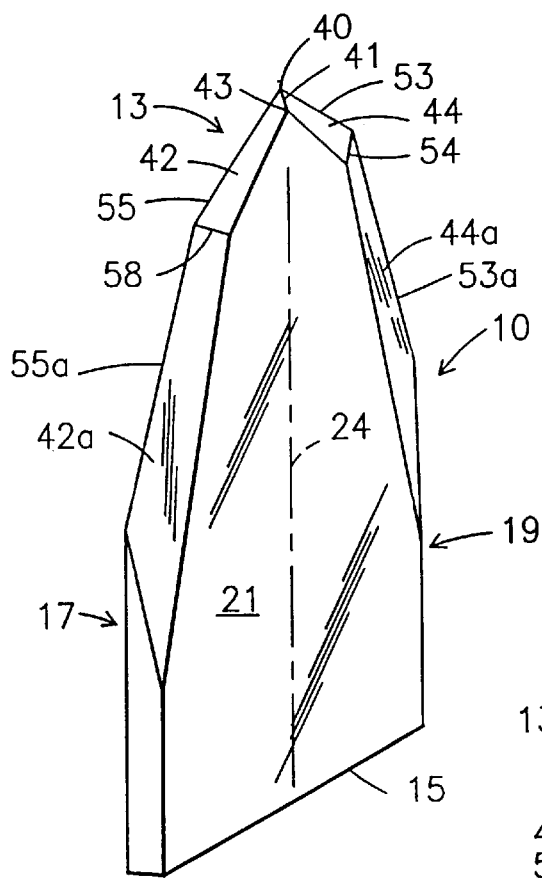
FIG. 6 is a perspective view of another embodiment of the inventive blade.
Figure 7:
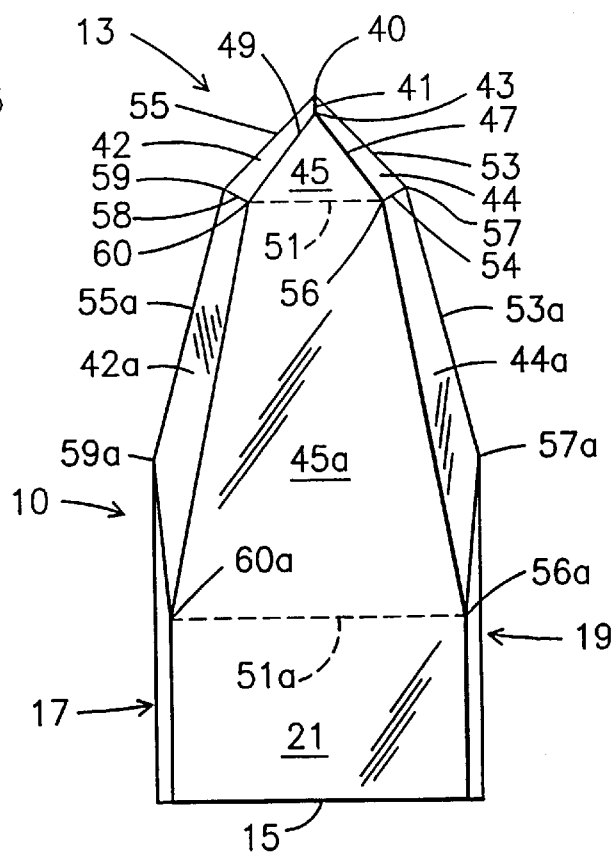
FIG. 7 is a top view of the inventive blade shown in FIG. 6.

Referring to FIGS. 1–10, a blade in accordance with the teachings of the present invention is generally designated by the reference numeral 10 and is seen to include a proximal end 11 and a distal end 13. The proximal end 11 is generally rectangular cubic having a proximal end surface 15, side edges 17 and 19, a top surface 21 and a bottom surface 23.

With particular reference to FIGS. 5 and 10, the side edges 17 and 19 are each composed of two angled surfaces. Thus, the side edge 17 includes an upper surface 25 and a lower surface 27 that meet an unsharpened elongated linear apex 29. The side edge 19 similarly includes an upper surface 31 and a lower surface 33 that meet at an unsharpened elongated linear apex 35.

The distal end 13 of the blade 10 includes a distal pointed tip 40 that is located "in space" between planes defined by the top surface 21 and the bottom surface 23. An edge 41 extends proximally in alignment with the central axis of elongation 24 of the blade 10 from the tip 40 to a proximal termination thereof 43 that lies in the plane of the top surface 21 and forms the apex of a triangular surface 45 defined by proximal edges 47 and 49 and the dotted line 51 for the embodiment of FIGS. 1–5, and 51a for the embodiment of FIGS. 6–10 depicting the additional cutting surfaces 42a and 44a. The surface 45 is coplanar with and extends from the top surface 21.

With further reference to FIGS. 1–2 and 6–7, the distal tip 40 is defined, in part, by distal edges 53, 55 that have respective proximal terminations 57 and 59, respectively. A segment 58 (FIGS. 2 and 7) extends proximally from the point 59 to a termination 60 at the left termination of the dotted line 51. Similarly, a segment 54 (FIGS. 2 and 7) extends proximally from the point 57 to a point 56 forming the right-hand termination of the dotted line 51. The edge 41 along with the edges 55, 49 and the segment 58 form a first angled cutting surface 42 whereas the edge 41 along with the edges 53 and 47 and the segment 54 form a second angled cutting surface 44. As depicted in the FIGS. 6–7 embodiment of the present invention with additional cutting surfaces 42a and 44a, cutting edges 55, 49, 53, 47 extend laterally and proximally from respective points 59, 60, 57, 56 to respective proximal termination points 59a, 60a, 57a, 56a. The proximal termination 59 connects to a short segment 61 (FIG. 3) having a proximal termination at 63 that lies in the plane of the bottom surface 23. Similarly, a short segment 65 (FIG. 3) interconnects between the proximal termination 57 of the edge 53 and a point 67 lying in the plane of the bottom surface 23. In the FIGS. 6–7 embodiment, the proximal terminations 59a, 57a connect to respective short segments 61, 65 having proximal terminations at respective points 63, 67 that lie in the plane of the bottom surface 23. The points 63 and 67 are interconnected by facet line 69 shown in FIGS. 3 and 8, the line 69 defining the predetermined location of the change in facet surface angle of the bottom surfaces 71 and 23, such that a second generally triangular or polygonal surface 71 is defined by the edges 53, 55, 61, 65 and the line 69 (FIG. 3) or 53, 55, 53a, 55a, 61, 65, and the line 69 (FIG. 8).

In the preferred embodiments of the present invention, the following specifications and dimensions are followed:

(1) The surfaces 42 and 44 each make an angle with respect to the bottom surface 23 and generally triangular or polygonal surface 71 of approximately 15° to 50° with the range of 20° to 27° being preferred.

(2) The plane of the generally triangular or polygonal surface 45, 45a defines an angle with the plane of the generally triangular or polygonal surface 71 of approximately 1° to 10°.

(3) The edges 53 and 55 make an angle therebetween as defined at the distal termination point 40 of 40° to 140° for the FIG. 1 embodiment; the edges 53 and 55 make an angle therebetween as defined at the distal termination point 40 of 10° to 60° for the FIG. 8 embodiment while the edges 53a and 55a in this embodiment make an angle therebetween of 40° to 140° about the central axis of elongation 24.

(4) Concerning the side edges 17 and 19, the surfaces 25 and 27 form an angle therebetween of 95° to 160° with an angle of 120° being preferred. Similarly, the surfaces 31 and 33 form an angle therebetween of 95° to 160° with an angle of 120° being preferred.

(5) The preferred width of the inventive blade 10 between the apices 29 and 35 is 0.8 to 7.0 millimeters.

(6) The thickness of the inventive blade 10 between the top surface 21 and the bottom surface 23 is from 90 to 625 microns.

The inventive blade 10 may be made of any suitable material including, for example, diamond, stainless steel, sapphire, ruby, cubic zirconia, pure or composite ceramics, ceramic metal composites and titanium alloys.

Where the material from which the blade is made is metal, i.e., stainless steel or a titanium alloy, the blade is suitably coated on both sides with a material that is dissimilar to the blade material but harder than the blade material. The coating should have zero porosity, strong adhesion to the substrate surface, fracture resistance, insolubility in typical cleaning solutions, and non-reactivity with respect to body tissues and chemicals. The coating material should be sufficiently resilient, corrosion resistant and biocompatible. The coating on the surgical blade may be applied by chemical or physical vapor deposition; flame deposition; sputtering; ion plating; ion, neutral or electron beam deposition; surface conversion; pulsed laser deposition; vapor jet deposition; molecular beam epitaxy or lamination with heat and/or pressure after which the blade is sharpened on one side of each edge only. The tip of the cutting, edge is then composed of the hard coating honed to a sub-micron edge radius of less than 0.1 micron.

The coating that may be applied to a metallic blade substrate may be any one of the following: titanium nitride, titanium carbide, titanium carbide-nitride, chromic oxide, high purity chrome, amorphous diamond with a hardness of at least 2000 Vickers, aluminum oxide, boron nitride, silicon carbide or silicon nitride. Where the substrate is made of stainless steel or a titanium alloy, it is sometimes appropriate to provide the coating in two layers. Thus, in this example, it might be appropriate to first coat a layer of titanium carbide on the metal substrate and, thereafter, apply a coating of amorphous diamond with a hardness of at least 2000 Vickers over the titanium carbide layer.

A preferred method employed to hone the precise edge on the blade is to secure the blade in a holding fixture at a fixed or adjustable angle and/or index. The blade edge is then lowered onto a lapping wheel, consisting of a rotating disk, the contact surface of which contacts or bears a substance that by abrasion, plastic flow, chemical dissolution, or any combination thereof removes both the coating and substrate. The rate of removal of both coating and substrate should be similar.

The cutting edge of the blade may be oriented perpendicular into the disk or obliquely into the disk, during honing. The holding fixture should exert just enough pressure on the cutting edge to keep the blade from skipping, but not so much pressure as would cause fracture of the cutting edge or bending of the blade. The lapping unit should be set up to minimize vibrations exerted on the blade from the cutting disk and holding fixture by using a precisely ground lapping disk and fixturing devoid of play in the fastened and moving parts. The lapping disk may be used such that the blade is lapped on the flat side, outer diameter or inner diameter.

The cutting edges should preferably be lapped to a minimum standard of 50× magnification chip-free under transmitted light in order to be acceptable for precise surgical applications. The blade is initially examined at 10 to 20× magnification to monitor and adjust the orientation of the blade edge on the disk. Then, when correct orientation is achieved, the edges are lapped and checked under an inspection scope at 50× magnification or higher.

The edge sharpening is completed when it meets these required specifications. After all edges have been suitably lapped, the blade is taken out of the lapping fixture, cleaned to remove residual chemicals, abrasive dust, and grinding swarf by rinsing with a solvent, gentle wiping with a soft, uniform material, or through ultrasonic cleaning.

Figure 12:
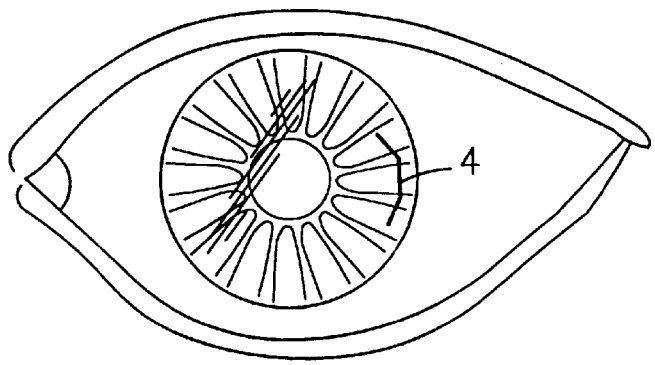
FIG. 12 is a front view of an eye with a slit formed by a prior art blade formed therein.

FIG. 12 shows an incision 4 performed through the use of a prior art ophthalmic surgical blade. Of note is the arcuate frown-like shape of the incision 4.

Figure 11:
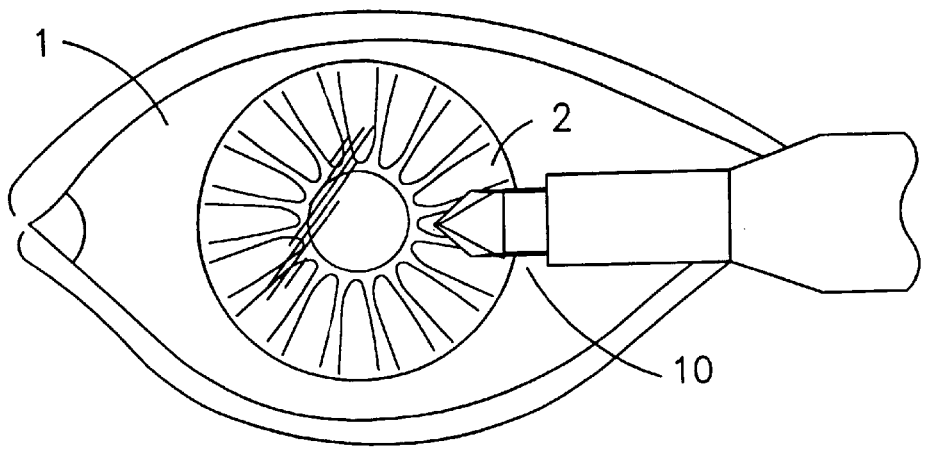
FIG. 11 is a front view of an eye with the inventive blade cutting a slit therein.
Figure 13:
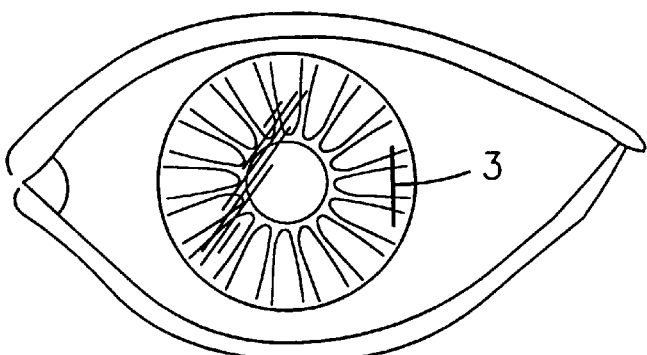
FIG. 13 is a front view of an eye with a slit formed through the procedure illustrated in FIG. 11 being formed thereby.

FIG. 11 shows a blade in accordance with the teachings of the present invention inserted within the cornea 2 of an eyeball 1. The resultant incision 3 is depicted in FIG. 13 and, as is shown, is straight. In this regard, it should be understood that the unsharpened side edges 17, 19 merely guide movements of the blade 10 into and out of the incision formed by the distal end 13 thereof. These unsharpened side edges 17, 19 prevent deformation of the eye tissues, prevent inadvertent tearing or widening of the lateral extremities of the incision, and avoid tearing of the epithelial tissue. The triangular surface 45 or polygonal surface 45, 45a coplanar with the top surface 21 provides a reference plane permitting the surgeon to make a straight incision. The triangular or polygonal surface 71 slightly angled with respect to the bottom surface 23 provides a reference plane permitting cutting of a groove.

As compared to the prior art, the inventive blade 10 is thinner near the tip 40 making the initial incision less expansive than is the case with prior art blades. Unlike skewed facet-style blades with parallel sharp lengthwise sides, the inventive blade 10 with unsharpened sides 17 and 19 can easily be repaired by simply re-lapping the facets near the tip of the blade on the top and bottom, which facets comprise the generally triangular or polygonal surfaces 45, 45a and 71. There are no sharp edges that could be damaged or that would require re-lapping. Thus, re-sharpening of the inventive blade does not result in loss of blade width. Use of the hard coating on a metal substrate dramatically increases blade life from the usual two to six uses before disposal.

As such, an invention has been disclosed in terms of a preferred embodiment thereof which fulfills each and every one of the objects of the invention as set forth herein above and provides a new and useful ophthalmic surgical blade having hard single bevel edges of great novelty and utility.

The invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in the limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. An ophthalmic surgical blade comprising:
   a thin elongated body having a proximal end and a distal end and a central axis of elongation;
   the proximal end including top and bottom flat parallel surfaces;
   the distal end having a single beveled edge blade portion including:
      a sharp tip lying in alignment with the axis of elongation and lying between the top and bottom surfaces;
      cutting edges extending laterally and proximally from the tip, the cutting edges defining an angle therebetween of 40° to 140°;
      angled cutting surfaces extending proximally from the cutting edges and extending proximally toward the top surface, each of the cutting surfaces defining an angle with the bottom surface of 15° to 50°;
      a generally triangular surface extending from an apex at the tip and proximally diverging to a location of merger with the bottom surface, the generally triangular surface defining an angle with the top surface of 1° to 10°; and
   the body having unsharpened side edges including two elongated guide surfaces meeting at an unsharpended apex, the guide surfaces defining an angle of 95° to 160°.

2. The ophthalmic surgical blade according to claim 1, wherein the cutting edges define an angle therebetween of 80°.

3. The ophthalmic surgical blade according to claim 1, wherein each of the cutting surfaces defines an angle with the bottom surface of 20° to 27°.

4. The ophthalmic surgical blade according to claim 1, wherein the top surface includes a further generally triangular surface extending from an apex just proximal of the tip and proximally diverging therefrom.

5. The ophthalmic surgical blade according to claim 1, wherein the angle between the guide surfaces is 120°.

6. The ophthalmic surgical blade according to claim 1, wherein the proximal end of the blade is rectangular cubic.

7. The ophthalmic surgical blade according to claim 1, wherein the top and bottom surfaces are spaced apart a distance of 90 to 625 microns.

8. The ophthalmic surgical blade according to claim 1, wherein the side edges are spaced apart a distance of 0.8 to 7.0 millimeters.

9. The ophthalmic surgical blade according to claim 1, wherein the blade is made of either stainless steel or a titanium alloy.

10. The ophthalmic surgical blade according to claim 9 further including a coating chosen from the group consisting of titanium nitride, titanium carbide, titanium carbide-nitride, chromic oxide, chrome, aluminum oxide, boron nitride, silicon carbide, silicon nitride and amorphous diamond.

11. The ophthalmic surgical blade according to claim 9 further including a coating consisting of a first layer of titanium carbide and a second layer of amorphous diamond.

12. The ophthalmic surgical blade according to claim 1, wherein the blade is made of a material chosen from the group consisting of diamond, sapphire, ruby, cubic zirconia, and pure or composite ceramics.

13. An ophthalmic surgical blade comprising:
   a thin elongated body having a proximal rectangular cubic end and a distal end and a central axis of elongation;
   the proximal end including top and bottom flat parallel surfaces spaced apart 90 to 625 microns;
   the distal end having a single beveled edge blade portion including:
      a sharp tip lying in alignment with the axis of elongation and lying between the top and bottom surfaces;
      cutting edges extending laterally and proximally from the tip, the cutting edges defining an angle therebetween of 80°;
      angled cutting surfaces extending proximally from the cutting edges and extending proximally toward the top surface, each of the cutting surfaces defining an angle with the bottom surface of 20° to 27°;
      a generally triangular surface extending from an apex at the tip and proximally diverging to a location of merger with the bottom surface, the generally triangular surface defining an angle with the top surface of 1° to 10°; and
   the body having unsharpened side edges including two elongated guide surfaces meeting at an unsharpened apex defining an angle of 120°, the apices of the side edges being spaced apart 0.8 to 7.0 millimeters.

14. The ophthalmic surgical blade according to claim 13 wherein the blade is made of either stainless steel or a titanium alloy.

15. The ophthalmic surgical blade according to claim 14 further including a coating chosen from the group consisting of titanium nitride, titanium carbide, titanium carbide-nitride, chromic oxide, chrome, aluminum oxide, boron nitride, silicon carbide, silicon nitride and amorphous diamond.

16. The ophthalmic surgical blade according to claim 14 further including a coating consisting of a first layer of titanium carbide and a second layer of amorphous diamond.

17. The ophthalmic surgical blade according to claim 13, wherein the blade is made of a material chosen from the group consisting of diamond, sapphire, ruby, cubic zirconia, and pure or composite ceramics.

18. An ophthalmic surgical blade comprising:
a thin elongated body having a proximal end and a distal end and a central axis of elongation;
the proximal end including top and bottom flat parallel surfaces;
the distal end having a single beveled edge blade portion including:
a sharp tip lying in alignment with the axis of elongation and lying between the top and bottom surfaces;
cutting edges extending laterally and proximally from the tip to a predetermined point at the distal end and the cutting edges defining an angle therebetween of 10° to 60°;
the cutting edges extending laterally and proximally from the predetermined point at the distal end, the extended cutting edges defining an angle therebetween of 40° to 140° about the central axis of elongation;
angled cutting surfaces extending proximally from the cutting edges and extending proximally toward said top surface, each of the cutting surfaces defining an angle with the bottom surface of 15° to 50°;
a generally polygonal surface extending from an apex at the tip and proximally diverging to a location of merger with the bottom surface, the generally polygonal surface defining an angle with the top surface of 1° to 10°; and
the body having unsharpened side edges including two elongated guide surfaces meeting at an unsharpended apex, the guide surfaces defining an angle of 95° to 160°.

19. The ophthalmic surgical blade according to claim 18, wherein the extended cutting edges define an angle therebetween of 80° about the central axis of elongation.

20. The ophthalmic surgical blade according to claim 18, wherein each of the cutting surfaces defines an angle with the bottom surface of 20° to 27°.

21. The ophthalmic surgical blade according to claim 18, wherein the top surface includes a further generally polygonal surface extending from an apex just proximal of the tip and proximally diverging therefrom.

22. The ophthalmic surgical blade according to claim 18, wherein the angle between the guide surfaces is 120°.

23. The ophthalmic surgical blade according to claim 18, wherein the proximal end of the blade is rectangular cubic.

24. The ophthalmic surgical blade according to claim 18, wherein the top and bottom surfaces are spaced apart a distance of 90 to 625 microns.

25. The ophthalmic surgical blade according to claim 18, wherein the side edges are spaced apart a distance of 0.8 to 7.0 millimeters.

26. The ophthalmic surgical blade according to claim 18, wherein the blade is made of either stainless steel or a titanium alloy.

27. The ophthalmic surgical blade according to claim 26 further including a coating chosen from the group consisting of titanium nitride, titanium carbide, titanium carbide-nitride, chromic oxide, chrome, aluminum oxide, boron nitride, silicon carbide, silicon nitride and amorphous diamond.

28. The ophthalmic surgical blade according to claim 26 further including a coating consisting of a first layer of titanium carbide and a second layer of amorphous diamond.

29. The ophthalmic surgical blade according to claim 18, wherein the blade is made of a material chosen from the group consisting of diamond, sapphire, ruby, cubic zirconia, and pure or composite ceramics.

30. An ophthalmic surgical blade comprising:
a thin elongated body having a proximal rectangular cubic end and a distal end and a central axis of elongation;
the proximal end including top and bottom flat parallel surfaces spaced apart 90 to 625 microns;
the distal end having a single beveled edge blade portion including:
a sharp tip lying in alignment with the axis of elongation and lying between said top and bottom surfaces;
cutting edges extending laterally and proximally from the tip to a predetermined point at the distal end and the cutting edges defining an angle therebetween of 10° to 60°;
the cutting edges extending laterally and proximally from the predetermined point at the distal end, the extended cutting edges defining an angle therebetween of 80° about the central axis of elongation;
angled cutting surfaces extending proximally from said cutting edges and extending proximally toward the top surface, each of the cutting surfaces defining an angle with the bottom surface of 20° to 27°;
a generally polygonal surface extending from an apex at the tip and proximally diverging to a location of merger with the bottom surface, the generally polygonal surface defining an angle with the top surface of 1° to 10°; and
the body having unsharpened side edges including two elongated guide surfaces meeting at an unsharpened apex defining an angle of 120°, the side edges being spaced apart 0.8 to 7.0 millimeters.

31. The ophthalmic surgical blade according to claim 30 wherein the blade is made of either stainless steel or a titanium alloy.

32. The ophthalmic surgical blade according to claim 31 further including a coating chosen from the group consisting of titanium nitride, titanium carbide, titanium carbide-nitride, chromic oxide, chrome, aluminum oxide, boron nitride, silicon carbide, silicon nitride and amorphous diamond.

33. The ophthalmic surgical blade according to claim 31 further including a coating consisting of a first layer of titanium carbide and a second layer of amorphous diamond.

34. The ophthalmic surgical blade according to claim 30, wherein the blade is made of a material chosen from the group consisting of diamond, sapphire, ruby, cubic zirconia, and pure or composite ceramics.

* * * * *